United States Patent [19]

Sinclair et al.

[11] Patent Number: 5,589,897
[45] Date of Patent: Dec. 31, 1996

[54] METHOD AND APPARATUS FOR CENTRAL VISUAL FIELD MAPPING AND OPTIMIZATION OF IMAGE PRESENTATION BASED UPON MAPPED PARAMETERS

[75] Inventors: Stephen H. Sinclair, 1208 Henry La., Gladwyne, Pa. 19035; Jonathan Nissanov, Philadelphia; Amitabba Gupta, Pittsburgh, both of Pa.

[73] Assignee: Stephen H. Sinclair, Gladwyne, Pa.

[21] Appl. No.: 576,859

[22] Filed: Dec. 22, 1995

Related U.S. Application Data

[63] Continuation of Ser. No. 432,015, May 1, 1995, abandoned.
[51] Int. Cl.$^6$ .................................................. A61B 3/02
[52] U.S. Cl. .......................... 351/223; 351/237; 351/239
[58] Field of Search ................................. 351/223, 222, 351/239, 237, 246, 243

[56] References Cited

U.S. PATENT DOCUMENTS

| | | |
|---|---|---|
| 3,993,976 | 11/1976 | Ginsburg . |
| 4,365,873 | 12/1982 | Ginsburg . |
| 4,405,216 | 9/1983 | Nadler et al. ......................... 351/237 |
| 4,426,663 | 1/1984 | Evans et al. . |
| 4,550,990 | 11/1985 | Trispel et al. . |
| 4,737,024 | 4/1988 | Damato . |
| 4,789,234 | 12/1988 | Ginsburg et al. . |
| 4,798,456 | 1/1989 | Enoch et al. . |
| 4,800,404 | 1/1989 | Ginsburg et al. . |
| 4,836,670 | 6/1989 | Hutchinson . |
| 4,859,052 | 8/1989 | McFarland et al. . |
| 4,927,259 | 5/1990 | Weber . |
| 4,971,434 | 11/1990 | Ball . |
| 4,995,717 | 2/1991 | Damato . |
| 5,011,649 | 4/1991 | Ginsburg et al. . |
| 5,060,062 | 10/1991 | Dotson . |
| 5,061,060 | 10/1991 | Aulhorn et al. . |
| 5,100,328 | 3/1992 | Badgley . |
| 5,159,927 | 11/1992 | Schmid . |
| 5,206,671 | 4/1993 | Eydelman et al. . |
| 5,216,458 | 6/1993 | Andrea et al. . |
| 5,270,750 | 12/1993 | Aulhorn et al. . |
| 5,287,507 | 2/1994 | Arden . |

OTHER PUBLICATIONS

Gordon Legge, Gary Rubin, Denis Peli, and Mary Schleske; Psychophysics Of Reading–II. Low Vision; Mar. 21, 1983; *Vision Res.* vol. 25. No. 2, pp. 253–266.

Gary Rubin, Kathleen Turano; Reading Without Saccadic Eye Movement; May 22, 1991; *Vision Res.* vol. 32, No. 5, pp. 895–902.

George Timberlake, Eli Peli, Edward Essock, Reed Augliere; Reading With A Macular Scotoma; *Investigative Opthamology & Visual Science*; Aug. 1987; pp. 1268–1274.

George Timberlake, Martin Manister, eli Peli, Reed Augliere, Edward Essock, and Lawrence Arend; Reading With A Macular Scotoma; *Investigative Opthalmology & Visual Science*; Jul. 1986; pp. 1137–1147.

Robert Massof, PhD.; Low Vision Enhancement: Vision For The Future; *Eyecare Technology*; Jan./Feb. 1994; pp. 32–35.

*Primary Examiner*—Hung Dang
*Attorney, Agent, or Firm*—Dowell & Dowell

[57] ABSTRACT

A method and apparatus for testing individuals having a sub-optimal central field of vision so as to identify areas within the visual field in which images can be perceived and for determining effects of contrast sensitivity and distortion within such areas such that visual images may be presented, after being enhanced so as to modify the images in accordance with tested parameters, so that the individual will perceive the images in an improved manner.

21 Claims, 3 Drawing Sheets

METHOD AND APPARATUS FOR CENTRAL VISUAL FIELD MAPPING AND OPTIMIZATION OF IMAGE PRESENTATION BASED UPON MAPPED PARAMETERS

This application is a continuation of application Ser. No. 08/432,015, filed May 1, 1995 now abandoned.

BACKGROUND OF THE INVENTION

1. Field of the Invention

This invention is directed to a method and apparatus for testing, assisting, and teaching persons having poor central vision and central or paracentral scotomas to enable them to read words and see complex figures or images. More specifically, the invention is directed to a method and apparatus for initially testing individuals so as to determine and map various parameters associated with the central or paracentral visual field to determine the area or areas of the individual's visual field which can be best utilized, the functional visual fields, for specific tasks, such as for receiving visual data presented in the form of letters or words for reading. Thereafter, the individual is further tested so as to identify what effect contrast sensitivity has in the selected functional visual field and to further determine the effect that illumination and/or color may have with respect to perception within the functional field. Further tests are made to identify distortions of images in the functional visual field. The information is preferably obtained through an interactive system wherein the individual reacts to different images displayed on a monitor or screen or other image transmitting device.

Having tested and mapped an individual's functional visual fields and the effect various parameters have on the fields, visual images are modified with appropriate enhancements so as to individualize the images to be presented depending upon the mapped parameters. The optimized images are thereafter presented to the functional visual field of the individual in such a manner so as to maximize the individual's ability to improve reading speed and comprehension.

The present invention further enables an individual's mapped parameters to be used to simulate a modified image so that others having normal vision can perceive what a person with poor vision actually sees, thus enabling others to understand the limitations which the individual has in understanding visually presented information.

2. History of the Related Art

Persons with macular, central retinal, pathology have difficulty with their central vision due to absences, scotomas, or other distortions. Previously, optical and closed-circuit television devices that have been used to assist such persons to read or recognize faces or objects at a distance have relied primarily upon magnification to overcome the visual impairment and have done little or nothing to account for individual parameters which affect the ability to comprehend images such as distortions and alterations of contrast sensitivity within the visual field. Recent research indicates that a person's ability to read or to recognize faces depends not only on the detection of elements, such as letters or objects, but also the spatial integration of these elements. For example, for a person to recognize the face of a friend, such person must have intact a sufficiently large area of their visual field, retinal area, to be able to see most of the features of the face at one time. For a person to read, a certain field of view is required without defects in order to integrate individual letters into words in between eye movements from one group of letters or words to another. Even if central acuity is good, if there are multiple paracentral visual field defects such that fewer than four letters can be spanned in the field of view at one time, a person's reading is incumbered because they are unable to integrate sufficient letters to form words and are unable to know where to shift their view to a subsequent group of letters or words.

People with central scotomas and poor central vision who must successfully adapt with conventional vision aids are those who develop stable eccentric fixation. That is, they turn their eyes away from an object thereby displacing the central scotoma out of the way so the object can be imaged onto the area of the intact and functioning retina. However, stable eccentric fixation is infrequently adopted by people who lose their central vision, most often the elderly, and when spontaneously adopted, may be inappropriate for a particular task. For example, if a person develops an eccentric fixation position for reading which leaves the scotoma to the right of a point of fixation, reading languages in the western world remains severely incumbered as the ability to follow a series of letters to form a word which can be comprehended continues to be a difficult, if not impossible, task.

Previously, visual fields were mapped primarily by glaucoma specialists interested in abnormalities of the far peripheral field, peripheral to 60°, or by neurologists interested in gross defects of the optic neural tracts, a quarter or half of the entire visual field missing. These fields have been mapped utilizing only points of light of varying intensity and size that are moved to the visual field from nonseeing areas or projected in sequence unto a curved or flat screen in front of an individual while the individual's vision is concentrated or focused straight ahead. The individual signals the observation of briefly presented eccentric light sources by pressing an appropriate device such as an electronic button.

In the Humphrey Automated Visual Field, points of light are sequentially presented at previously defined intercepts over the visual field in a random fashion. Each point is retested with progressively increased intensity until a person signals that a light is perceived, or if the light has been previously received, by gradually decreasing the intensity of the light until it is no longer perceived. The individual's sight must be fixed straight ahead on a central target which is a difficult task for persons with poor central field vision. Therefore, in order to test such persons an examiner has the patient look straight ahead at a stationary large target and evaluates the ability of fixation by periodically testing a physiologic blind spot which is a 15° eccentric scotoma in all persons. If a person responds to perception of light a significant number of times it is presented in the blind spot, there is an indication that fixation is unstable and that the field testing is unreliable. This is very common in individuals with central scotomas. However, by testing only points of light, the visual field is not evaluated for spacial integration or higher level processing that is required for visual tasks, such as character recognition in reading and facial recognition.

In another apparatus known as a scanning laser ophthalmoscope, a laser light is scanned rapidly over the retina in a raster pattern and is spatially attenuated in order to project, on the retina, spots or images of limited contrast and complexity. This instrument has been used in a limited manner to determine the ability of the retina to detect individual letters. The image is not stabilized on the retina; however, the examiner can view the retina simultaneously during the procedure so that a spot of light or image can be positioned in the retinal area of interest and any responses from the individual that occurred during unwanted eye movements, those away from a point of visual fixation, can be appropriately discarded. Unfortunately, this technique is laborious and has other severe restrictions.

The ability to perceive contrast centrally by an individual in relationship to spatial frequency has been previously tested by using letters of varying contrast or by using a sinusoidal gray scale grating projected on a monitor or screen or printed on a paper chart placed in front of the individual who looks directly at the letter or grating. The grating is usually presented at the central point of fixation in a circular area spanning 4°–5° of the central field. When letters are used, the contrast is varied up or down until the perception of each letter size is thresholded. If sinusoidal gratings are used, the contrast of light and dark bars against a background is varied until the individual signals that they are observed by indicating the orientation of the bars which are randomly presented at vertical, tilted left or right of vertical. The spacial distance or frequency is then changed by narrowing or widening the spacing between the bars, and the contrast is again varied until a threshold when the orientation of the grating is accurately perceived. The contrast sensitivity function for an individual is presented in a graph as a relationship between threshold contrast perceived at the center of fixation and the spacial frequency of the grating.

Conventionally, patients with retinal or optical nerve causes for reduced visual function frequently note that their vision is reduced under conditions of reduced illumination or that color affects their perception. Conventional testing for these parameters has been limited to measurements of central visual acuity at reduced light levels or with glare conditions or central fixation color matching or color image detection.

Heretofore, central visual field distortion has been subjectively evaluated by having a person visually fixate on the center of a grid of horizontal and vertical lines drawn on paper, known as an Amsler grid, as the person draws areas where there are distortion, such as waviness in lines. However, this technique is not quantitative and impossible to compare over time and does not lend itself to understanding an image in order to assist a patient with these encumbrances to comprehend information when presented.

In view of the foregoing, conventional methods of testing for poor central field vision have not taken into account the variety of secondary parameters which can affect an individual's limited vision within a functional field. Further, conventional methods of recreating and presenting information to individuals with poor central field vision have not recognized the need to modify images being presented so as to optimize the manner in which the images are received. Conventional methods have not incorporated contrast sensitivity, the effect illumination and/or color has on perception and the effect distortion has within a functional field of vision to modify image presentation and therefore have not been adequate to optimize the reception and comprehension of visual information.

SUMMARY OF THE INVENTION

This invention is directed to a method and apparatus for assisting and teaching individuals with poor central field vision to read and to recognize images which are normally not sufficiently perceived. In the methodology, a person is tested so as to determine and define a functional central visual field wherein high contrast images can be perceived. Having identified a functional field of vision, tests are made for other visual parameters which affect the ability of the person to comprehend visual images directed to the functional field. Further tests are made to measure contrast sensitivity within the functional field, to determine the effect of illumination or glare and/or color within the functional visual field and to detect and measure distortion in the functional visual field. With these parameters identified and mapped, it is then possible to enhance and modify a given image, such as a word, and present it to the person in a manner which is readily comprehensible.

With respect to one embodiment of the present invention, the individualized or optimized image can be recreated on a monitor, screen, or as a picture to enable people with normal vision to actually see what a person with poor central vision actually sees depending upon their visual parameters and thus understand the specific limitations that an individual may have in inputting, processing or comprehending visual information.

In the apparatus of the present invention, testing is preferably made utilizing an interactive system. A computer is used which is connected to a monitor, screen, or other viewing device which is sufficiently spaced relative to a person being tested so as to allow a test of the full 30° central visual field. The person being tested uses a joy stick, mouse or other input device, such as a voice detector, which is also connected into the computer, to respond to the presentation of complex images or symbols.

Once the tests have been made with respect to determining the functional visual field and the various parameters effecting the visual field, an image to be presented to a patient is placed into the computer and modified or enhanced so as to adjust the actual appearance of the image to account for the measured visual parameters. The computer is connected to a monitor or display screen, which may be a conventional television, which generates a visual presentation which is directed to the functional visual field of the retina in such a manner that images are capable of being perceived more distinctly than before being enhanced or modified. The enhanced images allow the patient to comprehend what is being presented more quickly, thus enabling more visual information to be provided over a shorter period of time.

It is a primary object of the present invention to provide a method for teaching individuals with poor central field vision to perceive and understand words and other visual images which are presented to them by subjectively modifying the words or images based upon the individuals' ability to receive images within their functional visual field.

It is also the object of the present invention to provide a method and apparatus for testing an individual having low central field of vision in such a manner as to determine specific functional areas for receiving complex visual information and thereafter identifying other visual parameters which may affect the defined functional areas so that such information may be used to create subjective visual presentations capable of being perceived when transmitted to the individual.

It is the further object of the present invention to provide a method for enabling individuals, who otherwise would never be able to read or comprehend visual images, to comprehend images which are presented in a modified format created subjectively so as to utilize each of the strengths of an individual's visual or optic system.

DESCRIPTION OF THE PREFERRED EMBODIMENT

Figure 1:
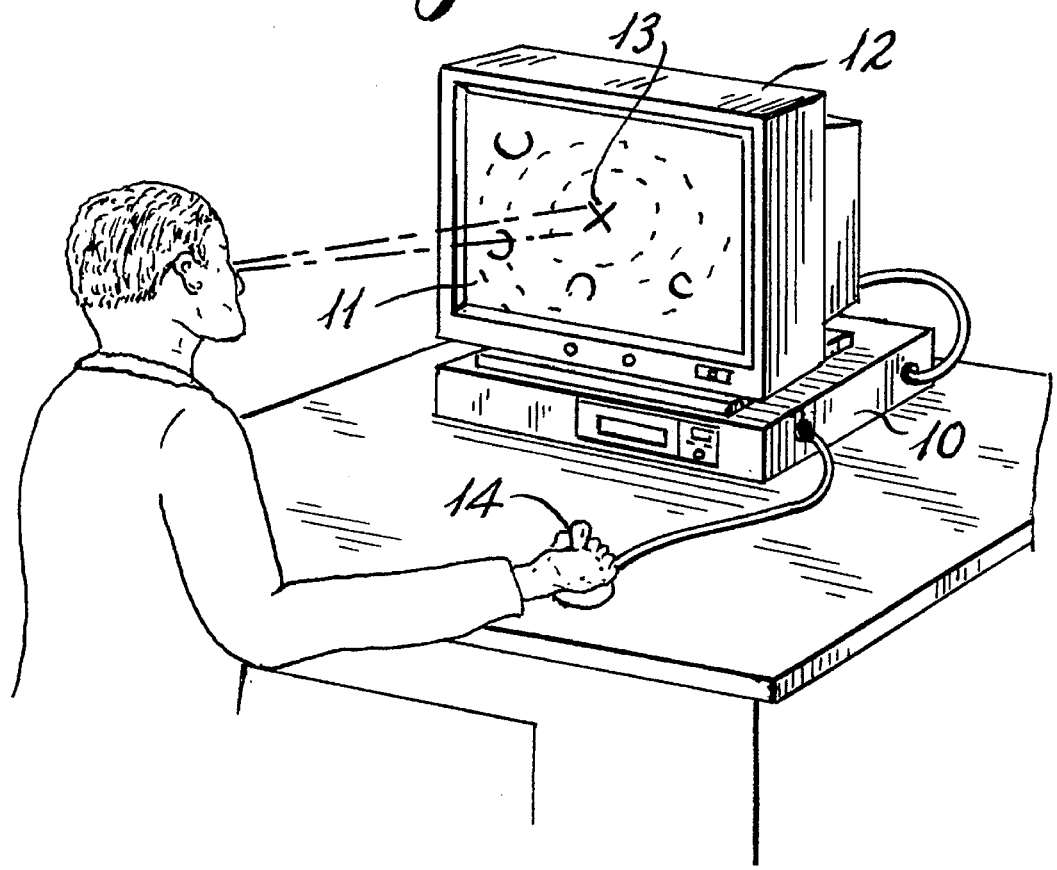
FIG. 1 is a perspective illustrational view showing an interactive testing apparatus for use in accordance with the teachings of the present invention.

In accordance with the present invention, it is first necessary to test a patient having impaired central field vision to determine a functional visual field in which high contrast images can be perceived. A computer 10 receives programming (by way of a diskette, CD-ROM, or other mass storage or communication medium) for presenting a series of quasi or pseudo-random images on a screen 11 of a monitor 12. The input program initially causes a fixation target 13 to be flashed or pulsated centrally of the monitor screen. With sufficient monitor resolution and screen size the fixation target can be maintained at the physical center of the screen. The target image, such as a star, cross, "X", or spot should be of a size that the patient can see the target even with poor central vision. It is desirable to test a 30° diameter visual field surrounding the target, however, the size of the field may be increased or decreased depending upon the size of the screen, the distance of the patient from the screen and the screen resolution. If the monitor is of insufficient size and resolution to test the entire 30° at one time, the fixation target would be programmed to flash at either the top, bottom, left or right side of the screen and, thereafter, either the inferior, superior right or left 15° of the visual field tested.

Each eye is normally tested separately although in some instances, to determine the binocular field of vision, both eyes may be tested simultaneously. Once the eye being tested is fixed upon the fixation target 13, the program projects a series of symbols at quasi or pseudo-random positions and orientations on the screen surrounding the fixation target, or to one side of the fixation target if the screen is small. Preferably, the images are in the form of a "C." The "C" is projected on the screen at various positions in the central 30° visual field that are eccentric to the fixation target (field intercepts) with the opening in the "C" oriented upwardly, downwardly, facing left or facing right. The size of the "C", the opening therein, and the thickness of the body of the "C" may be varied. The "C"'s are presented in high contrast either as white letters on a black monitor screen or dark letters on a light or lightly colored screen. The images are presented at maximum contrast for less than 0.2–0.4 seconds to prevent the patient's eye from drifting toward the briefly presented eccentric image. It is important for the validity of the test that the eye remain fixed on the fixation target 13.

The patient signals his or her perception of the orientation of the opening in the "C" utilizing a 4-way toggle switch, joy stick or other multi-axis input device or computer input method such as speech recognition to indicate the perceived orientation of that displayed "C" position. A multi-axis input device is manipulated forwardly, backwardly, left or right during the test. The size of the "C" at the various points of intercept are increased or decreased depending upon the patient's responses. Each point of intercept in the visual field is thresholded for the smallest size of "C" that is accurately perceived according to the patient's responses. In some instances, progressively larger images may be utilized until the "C" orientations are accurately perceived. In other instances, if the "C" is initially perceived, the size is gradually decreased until it is not accurately perceived by the patient. In this manner, it is possible to accurately map and define the eccentric functional visual field in which high contrast images are perceived by the patient. Generally 25 to 50 spaced field intercepts are tested for each patient.

Figure 2:
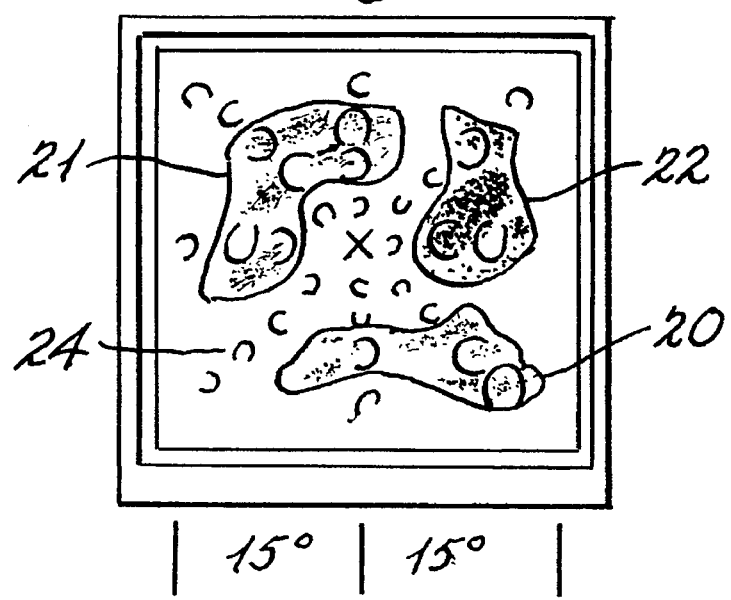
FIG. 2 is an illustrational plot reflecting the data obtained from the testing apparatus of FIG. 1.

As shown in FIG. 2, the data which results from the functional visual field evaluation is presented on a polar plot surrounding the fixation target as topographic isobars for the threshold of letter size that is accurately perceived at each of the points of intercept. The plot illustrates how the responses of the patient are used to indicate and determine which areas remain intact and are suitable to be considered functional in the central visual field. The "X" in the center of the illustration indicates the fixation target 13. The damaged or scarred areas of the retina are shown at 20, 21, and 22. The large "C"'s shown within area 22 reflect the threshold size of symbol perceivable by the patient during the test in that area of the tested field. This area of the field of vision is therefore inappropriate for receiving a sufficient number of understandable images to allow the patient to read. The area designated at 21 reflects that the "C"'s being perceivable are slightly smaller than in the area 22, however are still too large to allow receipt of useful images for purposes of reading or understanding visual presentations. The images or "C"3 s in the area shown at 20 are slightly smaller than in the area 21. However, the images are still too large to designate that portion of the field of vision, or the retina, as being a functional visual field. In the lower left hand quadrant are depicted a series of small images 24 which the patient responded to as being perceivable. It is these areas in which sufficient visual data can be received so as to be comprehensible in formulating word elements so as to enable the patient to effectively read images being presented. These areas are designated as the functional visual fields in accordance with the teachings of the present invention. In some instances, only one portion of the visual field may be satisfactory for receiving visual information and in other patients several areas may be adequate for use as functional visual fields.

It should be noted that the apparatus may be varied and still be within the teachings of the methodology of the present invention. For instance, as opposed to utilizing a computer monitor, the "C" images may be projected onto the inside of a curved hemispherical screen surrounding the head of the patient to thereby allow for testing of a greater peripheral visual field. In addition, it is also possible that the images may be projected unto the retina utilizing a scanning laser ophthalmoscope which modulates the intensity of a laser scanned across the retina.

As opposed to utilizing various orientations and sizes of "C" it is also possible to utilize images such as intricate letters such as P, Q, R and S which are displayed at the various points of intercept on the screen. When letters are used, it is preferred that the patient indicate recognition of a particular letter orally and the responses are inputted into the computer by microphone and analyzed by available speech recognition software. The size of the letters may be increased or decreased so as to threshold the size of letter which is comprehensible by the patient.

The central fixation of the patient on the target can be ensured by occasionally testing within the blind spot in which no image should be perceivable or, alternatively, by devices that monitor eye position, such as the infrared Ober II™ spectacles of Permobile can be used and testing suspended if the patient's fixation wanders beyond set limits (determined for each individual from measurements of the steadiness of fixation performed before the start of the field measurements).

Figure 3:
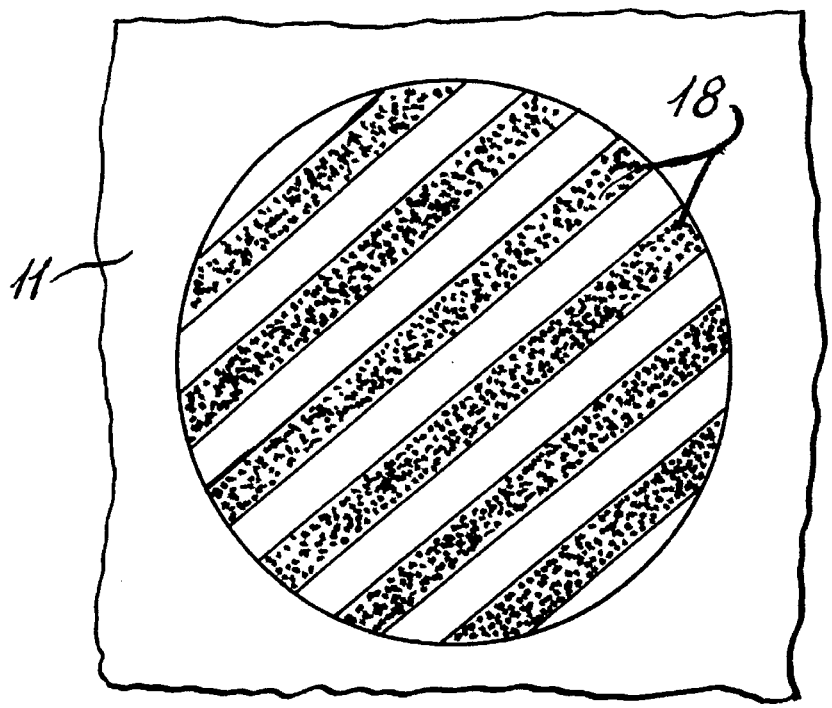
FIG. 3 is an enlarged view of a sinusoidal spot utilized in the testing procedure of the present invention.
Figure 4:
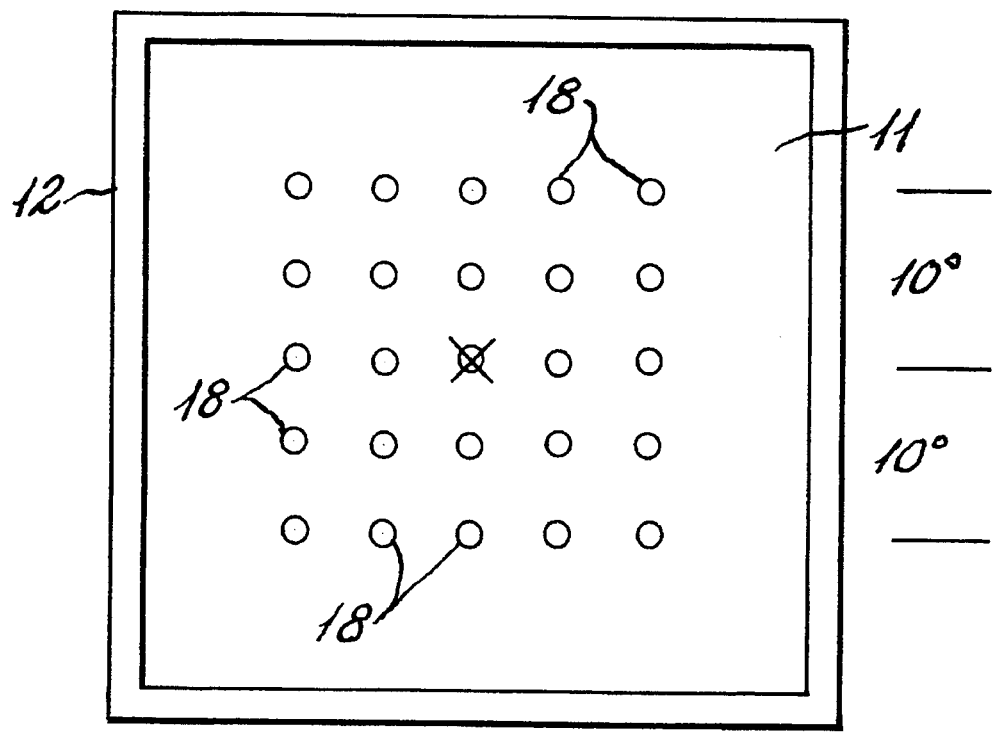
FIG. 4 is an illustrational view of a grid plan utilizing the sinusoidal spots shown in FIG. 3.

Having determined and mapped the functional field of vision for a given patient for perceived high contrast images, it is necessary to test and evaluate the effect contrast sensitivity has on the perception of images in the central visual field. In the present invention, "C" images or gratings are utilized to determine contrast sensitivity. As with the initial test, a flashing fixation target is utilized to attract central fixation and is large enough for the patient with poor vision to perceive. In the central 20° visual field letters or 4° spots of sinusoidal gratings 18, such as shown in FIG. 3, are used to measure the contrast sensitivity at a predetermined number of intercepts in the visual field 28. As shown in FIG. 4, approximately 25 intercept points are recorded in a grid of 5×5 visual field intercepts. The number of intercepts defining the grid may be increased or decreased, as desired, and the diameters of the visual field tested may be other than 20°. At each field intercept, which is tested randomly, the letter "C" or conversely a sinusoidal grating 18 in a spot of 4°–5° size is presented with varying contrast and with random orientation, being angled either left, vertically, or angled right. The patient signals his or her perception of the orientation of the "C" or the grating by deflecting the toggle switch 14 according to the direction of the opening in the "C" or the angle of the grating. Alternatively, the patient's verbal responses with respect to orientation may be recorded by voice recognition devices associated with the computer. After each point in the grid has been tested randomly, the sequence is repeated increasing or decreasing the contrast until a threshold is determined for perceiving the proper orientation depending upon the size of the image or grating. Utilizing the grating spots, the spatial frequency or spacing between the sinusoidal lines is varied so that a greater or lesser degree of background is projected through the image, thereby affectively changing the contrast of the image relative to the background. Generally only a few spatial frequencies, sizes of the "C" image or line grating spacings, are tested due to time constraints, as it is preferred to test at least 25 visual field intercepts for each patient.

The contrast sensitivity data is again presented as a graph or plot similar to FIG. 2 of the contrast sensitivity function at each point of the grid. This information may be directly compared to age-matched responses received from individuals having normal central field vision.

As with the previous test, the presentation of the "C"'s or sinusoidal gratings may be made utilizing a curved hemispherical screen surrounding the head of the patient on which the images are projected. In addition, scanning laser techniques may also be utilized to project images directly to the retina of the patient.

In some instances, it may be desired to determine the effect of luminance or color upon contrast sensitivity in the central 30° diameter visual field. In order to do this, during the test for contrast sensitivity, the luminance of the background or of the "C"'s or sinusoidal gratings may be varied such as by reducing the illumination levels or by varying the image and background colors at each of the field intercept points tested. At each field intercept, tested at random, the images of a particular size are presented with varying contrast and position. The patient signals perception of the orientation of the "C" or the sinusoidal grating by movement of the toggle switch. The information is again graphed and compared with age-matched responses received from individuals having normal central field vision.

Figure 5:
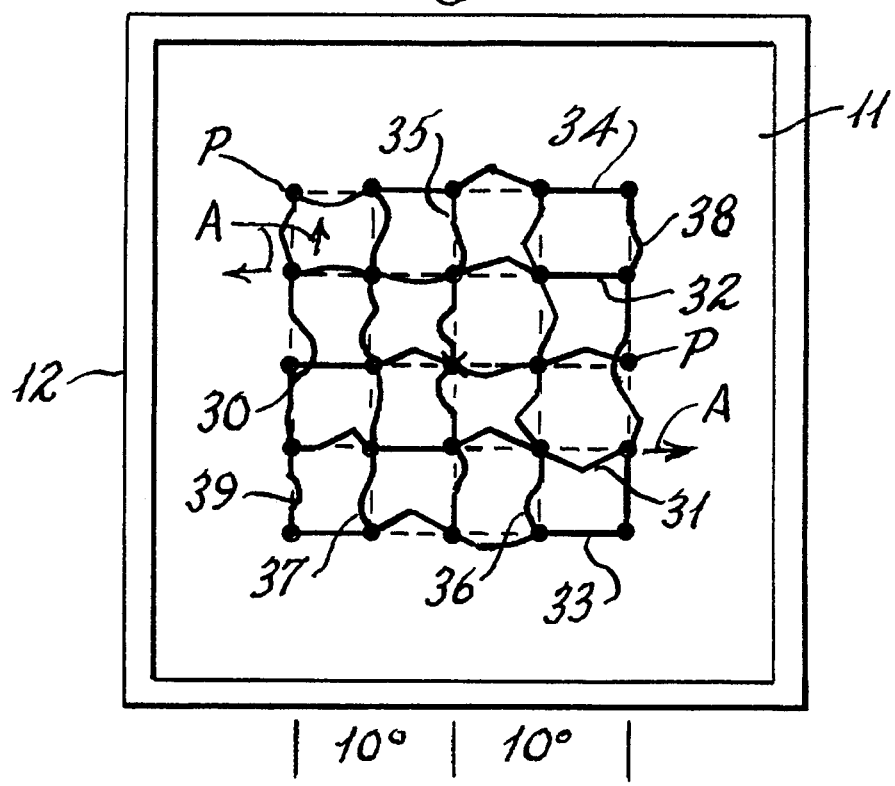
FIG. 5 is an illustrational view of a distortion sensing pattern utilized to sense visual distortions in accordance with the teachings of the present invention.

As an additional step in testing patients utilizing the teachings of the present invention, distortion within the functional central visual field is also measured. Again, utilizing the computer monitor of the previously described tests, the patient's line of sight is directed on the fixation target 13. With specific reference to FIG. 5, a horizontal line 30 is presented in high contrast on the screen through the center of the fixation target. The line should span the central 20° of the visual field and should be either black on a white background or vise-versa. The dimensions of the visual field tested may be increased or decreased. The line is presented initially with distortions along the length of the line which the patient is instructed to straighten. By use of a computer mouse, a patient can manipulate a cursor arrow "A" on the monitor to where the patient perceives deviation in the line. Utilizing the mouse, the patient can adjust the line to straighten the deviations perceived by positioning the arrow at the point of the deviation and clicking the mouse to take hold of the line and thereafter dragging the mouse so as to reposition the line to remove the distortion. The patient adjusts the line until all distortions are corrected as indicated by the dotted line segments in the drawing figure. Following the initial testing for field distortion, a second horizontal line 31 appears approximately 2° to 5° below or above the initial line of distortion. The patient is again instructed to reorganize the line until it is undistorted, as perceived. During the second phase of the test, the illumination or contrast between the line and the background may be varied to again assist in determining what effect illumination and/or color has with respect to the perception within the patient's functional visual field.

A third horizontal line 32 is then presented which is also spaced approximately 2° to 5° from the initial line and opposite the second line. The patient again is instructed to reorganize what are perceived to be distortions in the line. Additional horizontal lines 33 and 34 are presented sequentially below and above the group of three lines previously tested and the distortions removed by the patient while maintaining central fixation on the target 13. The group of all horizontal lines are then checked to ensure there are no distortions. The patient may also be instructed to ensure that the lines are evenly spaced and can move the lines relative to one another utilizing the mouse in a click and drag fashion.

Thereafter, a single vertical line 35 is presented through the fixation target which includes distortions which the patient must correct, as perceived. Once the first vertical line has been corrected, the illumination may be varied and a second vertical line 36 spaced 2°–5° from the first vertical line is presented for the patient to correct any distortions perceived. Additional vertical lines, 35–39, are sequentially presented in the same manner as discussed with respect to the horizontal lines. Although a series of five horizontal and vertical lines has been described, the number of lines may be increased or decreased depending upon a patient's visual condition. As opposed to moving the arrow or cursor "A" to the deviation of the line segment, the various points of intercept "P" of the grid shown in FIG. 5 may be used to straighten portions or sections of a line or of the grid. In these instances, the cursor would be moved over a particular point "P" and the computer mouse clicked to engage the point. Thereafter, the patient drags the intersection of the lines until the distortion in the grid is removed.

Figure 5A:
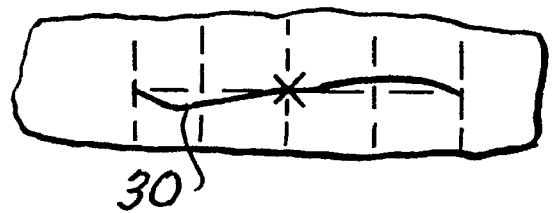
FIG. 5A is an illustration of one of the lines of distortion shown in FIG. 5 showing the actual appearance of a corrected distorted line to a person of normal vision.

When completed, the grid of horizontal and vertical lines with all distortions removed should appear straight to the patient. However, a person with normal vision, the grid appearing on the monitor will have distortions which represent the inverse of the individual distortion that the patient perceives in real life. An example is shown in FIG. 5A with respect to line 30. The patient corrected line, the dotted line, is now distorted in appearance to someone with normal vision. Quantitative measurements of these distortions can be made in terms of line spacing and the frequency and amplitude of each distortion as well as its location with the visual field.

At the completion of the three phase testing, the central visual field has been mapped with respect to high contrast elements. In addition, parameters which effect the perception within the functional visual field have also been determined and may be utilized to individualize information which is to be presented to a specific individual or patient. The information obtained may be evaluated so that areas can be selected for the presentation of letters, figures, or other complex images to the patient. Prior to presentation, the images are filtered or enhanced specifically for the individual's contrast sensitivity and perceived distortion measured in order to allow the patient to clearly perceive the images.

Text materials, numbers, figures or other images are electronically entered into the computer 10 by scanning, modem, CD-ROM, diskette or through other digital input or connection. The inputted material is reformatted and enhanced utilizing specially designed software to modify the normal appearance of the material to account for an individual's measured visual parameters. On the monitor screen a flashing fixation target similar to that previously discussed is utilized to attract central fixation of the individual. In this instance, however, the fixation target is positioned along the peripheral portion of the monitor screen so that the material is presented centrally on the screen at an appropriate eccentric locus or spacing corresponding to the location of the individual's intact functional vision which was previously determined from the mapping of the functional central visual field. High contrast letters are then presented in an appropriate size for the person to be able to integrate letters into words or objects into perceivable images. The eccentric locus where the material is displayed or presented is selected to allow the largest number of combined letters in a horizontal direction or the largest portions of an image to be simultaneously perceived. Preferably, at least four to five letters should be simultaneously perceivable by the patient. As previously discussed, the images or letters may be filtered to change the contrast depending upon the particular contrast sensitivity measured during testing. In addition, the images may be inversely distorted so as to correct for distortions measured during the testing process.

The computer can rapidly present sequences of letters or words from a text or other images which are presented from left to right or from right to left depending upon the language being read. If words contain letters greater than a number which are perceivable by the individual within his or her functional visual field, the words are interrupted or marked by dashes or asterisks or other symbols to signify a continuation of a given word. Preferably, the words can be broken into individual syllables. A variety of symbols may also be utilized to characterize the end of a paragraph or a particular portion of a written text so that an individual may scan the text.

As opposed to reading, it should be noted that other materials such as graphics and pictures may also be presented. Further, an individual may have the option of utilizing a mouse or other control device to regulate the positioning of an image on the screen as well as the timing of shifted images depending upon the ability to perceive material at a selected rate. Further, the images may be displayed not only on a computer monitor screen but may be broadcast or projected on other screens or conventional televisions.

Figure 6:
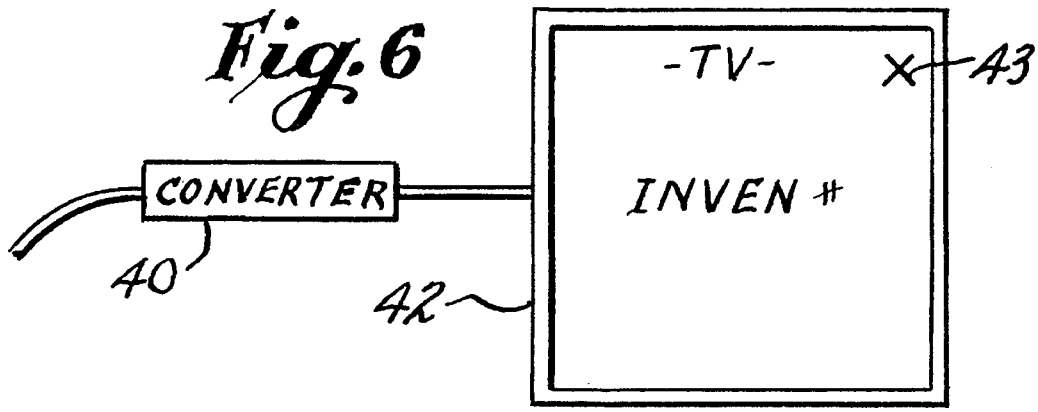
FIG. 6 is a prospective illustrational view of one form of apparatus for altering and displaying visual information which has been enhanced utilizing the data obtained through the testing procedures of the methodology of the present invention.

The teachings of the present invention may also be utilized to assist individuals with poor central field vision to receive and observe, in a comprehensive manner, programming which is available over conventional airwaves, cable or satellite or other similar video inputs. As shown in FIG. 6, an incoming signal is passed into a converter 40 wherein the signal is enhanced and modified depending upon the measured parameters discussed above. Such enhancing may include changing the luminance level of the incoming signal and modifying the size, orientation, or spatial characteristics of images created by the signal. The signals may also be modified to correct for distortions within the individual's functional visual field and to adjust color depending upon the individual's color sensitivity. The modified signal may thereafter be inputted to a conventional television 42 and displayed on the screen as a subjectively modified image or series of images with an appropriate fixation target being provided as shown at 43. The images on the television screen will not appear normal to individuals who have a normal field of vision as the images are specifically modified to allow an optimization of comprehension by the individual having poor central field of vision. As shown in drawing FIG. 6, the first two syllables of the word "invention" are displayed on the screen followed by a symbol such as an asterisk. This indicates to the person receiving the images that another syllable of the word is to follow, in this instance "tion". This is necessary for individuals who have a limited functional central visual field. The rate at which words or portion of words may be presented will be varied depending upon the individual patient. After time, it is possible for patients to increase their reading speeds and ability. It is also possible to allow the patient to regulate the rate at which information or images are provided on the screen. Although not shown in the drawing figures, the patient may be able to utilize a computer mouse and determine the rate of image presentation by the movement of the mouse relative to a support pad.

In view of the foregoing, the present invention also allows individuals with normal central field vision to actually see what a person having poor central field vision sees. Family members, patients, rehabilitation personnel, government licensing agencies and researchers may actually view material as it is perceived by individuals with vision abnormalities. Utilizing this insight, it should be possible for others to more completely understand the difficulties which individuals with vision abnormalities have in receiving visual information.

It is further contemplated that utilizing the teachings of the present invention that it should be possible to develop appropriate hardware and software to allow individuals with poor central field vision to accomplish other tasks which heretofore have not been possible due to visual limitations. This may include the ability for an individual to receive real time visual images using a helmet, glasses, or other devices wherein the real time visual image is modified to optimize the reception and comprehension of such images.

It will be appreciated by those skilled in the art that the present invention has been described with reference to specific structures and examples which are not intended as limitations, and which are but a few of the variations which are possible without departing from the spirit of the invention. Accordingly, the scope of the invention should be determined with reference to the appended claims.

We claim:

1. A method for optimizing the presentation of visual information to a person having a sub-optimal central field of vision comprising the steps of:

A. Determining the geometry of the person's central visual field with regard to perception of high contrast images;

B. Measuring parameters representative of contrast sensitivity of the person at a plurality of locations within the determined central visual field;

C. Measuring parameters representative of luminance sensitivity at a plurality of locations in the determined central visual field;

D. Measuring parameters representative of perceived spatial distortion of locations within the determined central visual field;

E. Modifying and enhancing the visual information in accordance with the measured parameters to create individualized visual information;

F. Presenting the individualized visual information to the person's functional areas of the central visual field.

2. The method of claim 1 including measuring parameters representative of color sensitivity at a plurality of locations in the determined visual field.

3. The method of claim 1 in which the measurement of the person's functional areas of the central visual field comprises pseudo-randomly displaying on a visual display device to the person a fixation target and a sequence of a plurality of directionally high contrast images at a plurality of predetermined locations within a radius from said fixation target, and recording images perceived by the person.

4. The method of claim 3 in which the images randomly appear at different orientations at said plurality of predetermined locations and recording image orientations perceived by the person.

5. The method of claim 4 in which the images are selected from a group of images including generally "C" shapes and gratings formed of a plurality of spaced line segments.

6. The method of claim 3 in which the images are intricate letters of the alphabet.

7. The method of claim 3 in which the images are selected from a group of images including generally "C" shapes and gratings formed of a plurality of spaced line segments.

8. The method of claim 3 in which the size of the image is decreased dependent upon the person's indicated correct perception of the orientation of the image at the random points of intercept until a threshold minimum image size is determined.

9. The method of claim 8 in which the points of intercept are spaced within the visual field to approximately 15° eccentrically from said fixation target.

10. The method of claim 9 in which the images are displayed for periods of up to approximately 0.4 seconds.

11. The method of claim 8 in which the contrast sensitivity of the person is measured by randomly displaying an image at predetermined visual field intercepts on the display screen and wherein the contrast and orientation of the image with respect to the display screen is randomly changed and wherein the person indicates perception of orientation each time an image is perceived on the display screen.

12. The method of claim 11 in which the image and background illumination of the display screen is varied as the image is presented.

13. The method of claim 12 in which the color of the display screen and the image are varied during presentation of the image.

14. The method of claim 13 in which a plurality of spaced horizontal and vertical distorted lines are presented on the display screen, and the person rearranging the lines where the lines appear to be distorted to thereby determine distortions within the person's central visual field.

15. The method of claim 14 in which said horizontal and vertical lines are spaced at approximately 2°–5° with respect to one another when measured radially outwardly from the fixation target.

16. A method for testing a person having a reduced central field of vision comprising the steps of:

A. Determining the person's functional visual field in which high contrast images are perceived including randomly displaying an image at a plurality of points of intercept on a display screen eccentric to a fixation target with the image randomly appearing at different orientations, and recording orientations perceived by the person;

B. Measuring parameters of the contrast sensitivity of the individual within the functional visual field by randomly displaying an image at predetermined visual field intercepts on the display screen and wherein the contrast and orientation of the image with respect to the display screen is randomly changed and wherein the person indicates perception of orientation each time an image is perceived on the display screen; and C. Measuring parameters for distortion of images in the functional visual field in which a plurality of spaced horizontal and vertical distorted lines are presented on the display screen, and the person rearranging the lines where the lines appear to be distorted to thereby determine distortions within the person's functional visual field.

17. The method of claim 16 in which the image is selected from a group of images including generally "C" shapes and gratings formed of a plurality of spaced line segments.

18. The method of claim 17 in which the size of the image is decreased dependent upon the person's indicated correct perception of the orientation of the image at the random points of intercept until a threshold minimum image size is determined.

19. The method of claim 18 in which the display screen is varied in background illumination as the image is presented.

20. The method of claim 19 in which the color of the display screen and the image are varied during presentation of the image.

21. An apparatus for testing a person having poor central field vision so as to determine functional visual fields for receiving images comprising; a computer means, a display monitor connected to said computer means said computer means, being operable to display a fixation target on said display monitor and to randomly display images on said display screen in eccentric relationship to said fixation target in random orientation, and to display images in a pattern on said screen wherein said images are randomly oriented, and to display a plurality of horizontal and vertical lines on said screen, and means responsive to a person's recognition of the images and lines on said screen for recording the person's perception of said images.

* * * * *